(12) United States Patent
Mihaylov et al.

(10) Patent No.: US 9,188,509 B2
(45) Date of Patent: Nov. 17, 2015

(54) SAMPLING DEVICE

(71) Applicant: Nextteq LLC, Tampa, FL (US)

(72) Inventors: Gueorgui M. Mihaylov, Virginia Beach, VA (US); Bryan I. Truex, Tampa, FL (US)

(73) Assignee: Nextteq LLC, Tampa, FL (US)

( * ) Notice: Subject to any disclaimer, the term of this patent is extended or adjusted under 35 U.S.C. 154(b) by 279 days.

(21) Appl. No.: 13/729,533

(22) Filed: Dec. 28, 2012

(65) Prior Publication Data

US 2013/0167667 A1 Jul. 4, 2013

Related U.S. Application Data

(60) Provisional application No. 61/580,831, filed on Dec. 28, 2011.

(51) Int. Cl.
*G01N 1/00* (2006.01)
*G01N 1/10* (2006.01)
*G01N 1/22* (2006.01)

(52) U.S. Cl.
CPC .. *G01N 1/00* (2013.01); *G01N 1/10* (2013.01); *G01N 1/22* (2013.01)

(58) Field of Classification Search
CPC ............ G01N 1/00; G01N 1/10; G01N 1/22; G01N 1/24; G01N 2001/241; G01N 2001/248
USPC ............... 73/864.51, 864.54, 864.62, 864.63, 73/864.91
See application file for complete search history.

(56) References Cited

U.S. PATENT DOCUMENTS

| | | | | | |
|---|---|---|---|---|---|
| 3,866,474 | A | * | 2/1975 | Hasselmann | 73/864.34 |
| 4,008,621 | A | * | 2/1977 | Ostojic et al. | 73/864.52 |
| 4,338,826 | A | * | 7/1982 | Jacoby et al. | 73/864.62 |
| 4,546,659 | A | * | 10/1985 | Gill et al. | 73/864.62 |
| 5,074,155 | A | * | 12/1991 | Vecere | 73/864.62 |
| 5,178,021 | A | * | 1/1993 | Kosuth | 73/864.62 |
| 5,411,482 | A | | 5/1995 | Campbell | |
| 5,437,201 | A | * | 8/1995 | Krueger | 73/864.35 |
| 6,148,914 | A | * | 11/2000 | Guieze | 166/264 |
| 8,714,035 | B2 | * | 5/2014 | Mihaylav et al. | 73/864.51 |
| 2004/0007590 | A1 | | 1/2004 | Hedington et al. | |
| 2009/0123093 | A1 | | 5/2009 | Lemoyne et al. | |
| 2011/0202031 | A1 | | 8/2011 | Mihaylov et al. | |
| 2011/0219891 | A1 | | 9/2011 | Mihaylov et al. | |

* cited by examiner

*Primary Examiner* — Daniel S Larkin
(74) *Attorney, Agent, or Firm* — Bernard G. Pike, Pike IP Law, PLLC

(57) ABSTRACT

Sampling devices are used to obtain samples of fluids to be analyzed and to determine the composition of the fluid in the sampled environment. A sampling apparatus with an inflatable sample bag used to collect and store liquid, air, vapor, and or gas samples by drawing the sample into the bag through an inlet, a sorbent tube, cassette, and/or other collection media is described. The means for extracting the sample and moving it into the sample bag comprises means for expanding the volume of a sample bag and creating a vacuum or reduced pressure within the sample bag. The means for expanding the include separating walls of a sample bag by use of gravity, pneumatic pressure, a biasing force, hydraulic force, for example or increasing the volume of a sample bag retaining container by such forces. Such sampling apparatuses do not require use of a sampling pump.

36 Claims, 8 Drawing Sheets

4-A  4-B  4-C

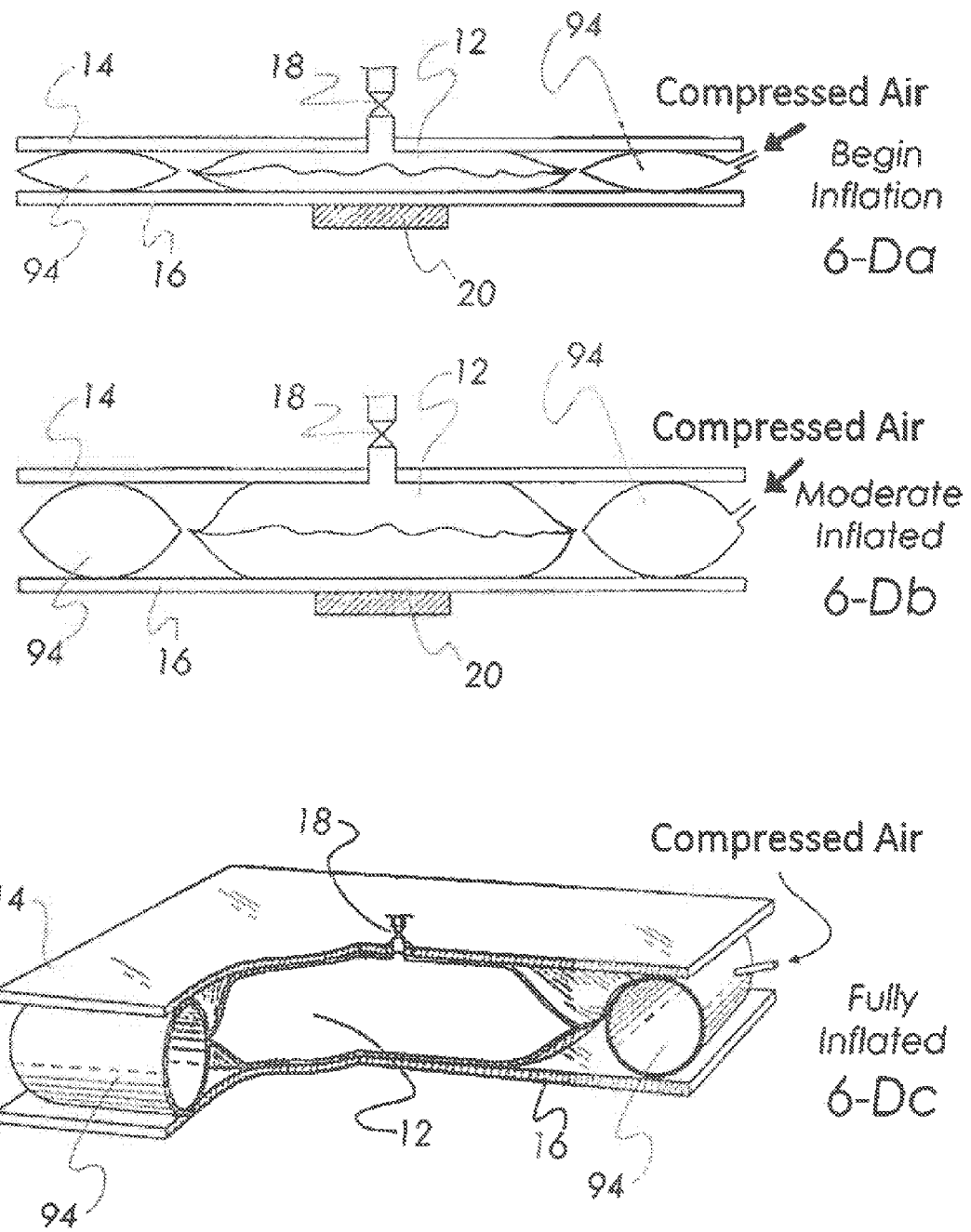
FIG.6(ext)

SAMPLING DEVICE

RELATED APPLICATIONS

This application claims priority under 35 U.S.C. 119 to U.S. Provisional Patent Application No. 61/580,831 filed on Dec. 28, 2011 which is hereby incorporated by reference in its entirety.

FIELD OF THE INVENTION

Sampling devices are used to obtain samples of fluids to be analyzed and to determine the composition of the fluid in the sampled environment. Sampling devices may be designed to obtain samples of a fluid at a particular moment or obtain a sample over an extended period of time. The sampling devices are designed to relatively easily obtain an accurate whole air sample and minimize contamination of the sample during the sampling process and during storage of the sample. Embodiments of the sampling device include an inflatable sample bag used to collect and or store air, vapor, and or gas samples and or used to collect liquid, air, vapor, and or gas samples on a sorbent tube, cassette or other collection media by drawing the liquid, air, vapor, and or gas sample through a sample bag inlet, the sorbent tube, cassette, and/or other collection media when the sample bag is inflated.

BACKGROUND

Fluid sampling is regularly performed to determine the amount of various target compounds in an area such as a chemical facility, a laboratory, confined space, or other area which could potentially be contaminated by chemical compounds. Samples may be taken over a short sampling period of time indicating "instantaneous" exposure of personnel to the compounds ("grab sample") or the sample taken over an extended sampling period of time to determine an average exposure of the personnel to the compound over the extended sampling period of time. Conventionally, samples are typically drawn into a sample bag by a sampling pump or collected on a cassette attached to the pump.

There are basically two conventional sampling systems, a direct sampling system and an indirect sampling system. A typical direct sampling system is shown in FIG. 1-A. As shown in FIG. 1-A, a conventional direct sampling apparatus or device 61 comprises a sampling pump 60 that draws a gas to be sampled from the surrounding environment and discharges the sampled gas through the tubing 65 into a sample bag 62. The sample bag 62 comprises an inlet 66 with a tubing connection. The inlet 66 may further be attached to a valve that may be opened during the sampling process and closed to retain the sample in the sample bag 62. The sample bag 62 may then be removed from the sampling device 61 and sent to a laboratory for analysis. In a direct sampling apparatus, the inlet of the sampling pump 60 is in fluid communication with the area to be sampled and the outlet of the pump 60 is in fluid communication with the inner volume of the sample bag 62. As such, the gas to be sampled flows through the sampling pump 60 and tubing 65. In such a direct sampling system, the gas contacts the internal components of the sampling pump 60 and the inner wall of the tubing 65, this contact may result in contamination of the sampled gas or loss of a portion of the sample as it attaches to or reacts with the material in the pump or with the walls of the tubing resulting in a sample that represents less than the actual concentration of the contaminant. The internal components of the pump and inner wall of the tubing may still comprise a residue of previously sampled gas or may be contaminated from a cleaning or maintenance procedures. To eliminate the chance of contamination of the sampled gas and/or loss of a portion of the components of the sampled by contact with the sampling pump or other components of the direct sampling apparatus, indirect sampling apparatuses may be used.

A typical indirect sampling apparatus is shown in FIG. 1-B. As shown in FIG. 1-B, a conventional indirect sampling apparatus 63 also comprises a sampling pump 60. However, the sampling pump 60 in an indirect sampling method draws air from inside a hermetically sealed box 64 (sometimes referred to as a "lung box") to create a vacuum. A lung box 64 is a rigid walled hermetically sealed box with a connector for the pump 60 inlet and a connector 65 to provide fluid communication between the sample bag 62 with the exterior area to be sampled. A sample bag 62 within the lung box 64 expands due to the vacuum and thus draws gas from the area to be sampled through tubing 65 into sample bag 62. The sample bag 62 in an indirect sampling system also comprises an inlet 66 with a tubing connection and a valve that may be opened during the sampling process and closed to retain the sample in the sample bag 62. The sample bag 62 may be removed from the lung box 64 and sent to a laboratory for analysis. As the pump draws air out of the lung box 64, the walls of the gas-sampling bag 62 are pulled apart by the resultant vacuum thus increasing the inner volume of the sample bag 62 and providing driving force for the ambient gas to be sampled to fill the sample bag 62. The indirect sampling apparatus 63 may be more bulky than a direct sampling apparatus 61 but provides a lower risk of contamination, cross-contamination of samples and/or loss of a portion of the contaminant. Drawbacks for both of the conventional direct and indirect sampling apparatuses include the necessity of carrying and storing bulky equipment, charging the pump batteries, maintaining and calibrating the pump regularly and calibrating the pump by trained personnel before and after use of the pump for time weighted average (TWA) samples, and to establish a clean stationary sampling place. Further, in certain applications such as, but not limited to, chemical, petrochemical, petroleum, and natural gas facilities, the electronic pumps of direct and indirect sampling apparatuses must be certified as intrinsically safe to ensure the electronic pump does not create a spark sufficient to cause an explosion or a fire.

The high prices of both direct and indirect sampling apparatuses and the ancillary equipment affect the overall cost of the sampling. These sampling apparatuses require that the sampling pump be well calibrated and can pump consistently particularly when performing a sampling process through an extended period.

A more sophisticated sampling apparatus includes a SUMMA Canister 70 as shown in FIG. 1-C. A SUMMA canister is a stainless steel vessel which has specially passivated internal surfaces using a "Summa" passivation process. A Summa passivation process combines an electro-polishing step with chemical deactivation to produce a surface that is chemically inert. Due to the passivation of the surface, chemical compounds are not absorbed on the surface and samples retained in a SUMMA canister are stable for a longer period than a sample retained in a conventional sample bag. To draw a sample into the canister, the pressure within the SUMMA canister 70 is reduced to vacuum of approximately twenty-eight inches mercury to remove substantially all the gas in the canister 70. The residual gas is typically uncontaminated air or ballast such as nitrogen or other inert carrier gas. The SUMMA sampling apparatus comprises a special flow regulator that may be calibrated to achieve predetermined sampling time of, for example, 15 minutes, 30 minutes, 1 hour, 2 hours or up to 24 hrs. The sampling process is typically finished when the pressure in the SUMMA canister has risen to about 2 inches of mercury vacuum; therefore, the canister is still under vacuum even after sampling. To facilitate withdrawal of the sample from the canister for analysis or other use, the SUMMA canister 70 must subsequently be pressurized with an inert carrier gas or filtered calibration grade clean air. The inert carrier gas or filtered calibration grade clean air raises the pressure within the SUMMA canister without contaminating the sample. However, adding gas in the pressurization process and the original gas in the canister after reducing the vacuum to 28 inches results in a dilution of the concentration of the target gases in the sample.

After pressurization, an aliquot volumetric analysis sample of the diluted gas is withdrawn for analysis. Each step including vacuuming, sampling, and pressurizing of the Summa canister is monitored by use of a pressure gauge and the accuracy of monitoring each step depends on the accuracy and reliability of the pressure gauge to calculate volumes of gas in the canister. In many cases, the pressure gauges used with SUMMA canisters do not have accuracy necessary or are not calibrated precisely enough for extremely accurate determination of the dilution ratio between the gas actually sample and the residual gas in the container and the gas added during the pressurization process. Therefore, there is an inherent systematic error in the gas concentration calculations and target gas analytical determination. As such, the accuracy of overall method is compromised from the many steps and is prone to errors.

The disadvantages of using a SUMMA canister sampling apparatus include the initial high costs of the canister, the high cleaning cost of the interior of the canister, high maintenance costs of the canister and peripheral equipment, the high cost of purchasing and maintaining a special cleaning system in specialized labs, the high cost of special gauges and expensive flow controllers, the necessity of a precise flow calibration for each extended sampling period, the necessity of constant observation during a sampling period to end the sampling process so the pressure does not exceed the limit of 2 inches of mercury vacuum, the necessity of accurately pressurizing the SUMMA canister with a carrier gas or filtered calibration grade clean air, the high cost of the inert carrier gas cylinder and cylinder demurrage or the cost of creating the filtered grade clean air, the necessity of performing additional calculations after chemical analysis, and the necessity to know the initial sampling conditions including temperature, barometric pressure, and altitude above sea level.

Due to drawbacks of the sampling apparatuses and processes described above, there is a need for a sampling apparatus which will eliminate at least a portion of the drawbacks of the conventional sampling methods.

There is an additional need for a device which will allow sampling for preset short sampling periods including 15 min., 30 min., 2 hrs. (STEL or Ceiling, r task-durations in some occasions) and/or extended sampling periods including 8 hours to 24 hours (TWA) without use of pumps and/or auxiliary vacuum equipment. There is a further need for a sampling apparatus that uses alternative sources of energy for the sampling process and which is easy to manufacture at low cost and easy to operate.

SUMMARY

Sampling systems are used to obtain samples that represent the environment from which the sample was taken. The components of the sampling systems should not significantly contaminate the sample. Embodiments of a sampling device may comprise a sampling bag and a means for extracting the sample from the environment and moving it into the sample bag. In one embodiment, the means for extracting the sample and moving it into the sample bag comprises means for physically expanding the volume of a sample bag and creating a vacuum or reduced pressure within the sample bag.

The means for physically expanding the volume of a sample bag and creating a vacuum or reduced pressure within the sample bag include separating walls of a sample bag by use of gravity, pneumatic pressure, a biasing force, hydraulic force, for example or increasing the volume of a sample bag retaining container.

In one embodiment, a sampling apparatus comprises a sample bag, a hanging element, and a force, such as the force of gravity exerted on a weight connected to the sampling bag, wherein the force created by the weight is sufficient to increase the inner volume of the sample bag and create a vacuum within the inner volume. The sample bag may further comprise panels, such as a top panel and/or a bottom panel, attached to the walls of the sampling bag. The sampling device may further comprise a flow control device in fluid communication with the inlet and a gas to be sampled. The flow control device may be a capillary tube or contain an orifice to control the flow rate into the sample bag. Still further, the flow control device may comprise a particulate filter 42. The sampling devices or apparatuses may further be activated by other forces including gravity, springs, biasing elements, compressed air, or hydraulic fluids.

Further embodiments of the sampling apparatus may include an indirect activation sampling device or apparatus comprising systems for activation by gravity, springs, biasing elements, compressed air, or hydraulic fluids.

The terminology used herein is for the purpose of describing particular embodiments only and is not intended to be limiting of the invention. As used herein, the term "and/or" includes any and all combinations of one or more of the associated listed items. As used herein, the singular forms "a," "an," and "the" are intended to include the plural forms as well as the singular forms, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof.

Unless otherwise defined, all terms (including technical and scientific terms) used herein have the same meaning as commonly understood by one having ordinary skill in the art to which this invention belongs. It will be further understood that terms, such as those defined in commonly used dictionaries, should be interpreted as having a meaning that is consistent with their meaning in the context of the relevant art and the present disclosure and will not be interpreted in an idealized or overly formal sense unless expressly so defined herein.

In describing the invention, it will be understood that a number of techniques and steps are disclosed. Each of these has individual benefit and each can also be used in conjunction with one or more, or in some cases all, of the other disclosed techniques. Accordingly, for the sake of clarity, this description will refrain from repeating every possible combination of the individual steps in an unnecessary fashion. Nevertheless, the specification and claims should be read with the understanding that such combinations are entirely within the scope of the invention and the claims.

BRIEF DESCRIPTION OF THE DRAWINGS

FIG. 1-B depicts a conventional indirect sampling apparatus for direct short or long term sampling comprising a variable speed pump connected to a hermetically sealed box with rigid walls and a sample bag within the box with inlet in fluid communication through one of the walls with the ambient air; FIG. 1-C depicts a conventional SUMMA canister apparatus with a fluid flow controller/regulator and pressure gauge;

FIG. 3-B depicts an embodiment of a sampling apparatus comprising a sample bag, a weight sufficient to create a vacuum within the inner volume; and a support element for supporting the panel; FIG. 3-C depicts an embodiment of a sampling apparatus comprising a sample bag, a weight sufficient to create a vacuum within the inner volume; and a hanging element comprising a top panel fitted as a lid to a plastic box;

FIG. 4-B depicts a sampling apparatus comprising a sampling bag with an accordion type side walls; and FIG. 4-C depicts a sampling apparatus comprising a sample bag with randomly folded side walls;

FIGS. 6-Ac and 6-B depict springs mounted on the exterior of the sample bag and biasing panels attached to or forming part of the sample bag walls; FIG. 6-C depicts the use of pressurized fluid in pneumatic or hydraulic cylinders to bias the panels attached to or forming part of the sample bag walls for activation of the sampling process; FIGS. 6-Da, 6-Db and 6-Dc illustrate a pressurized gas used with an inflatable body or bodies surrounding the sampling bag for biasing the sampling bag wall or the panels.

DESCRIPTION

Sampling devices and sampling apparatuses (used herein as "sampling device" or "sampling devices") are used to obtain samples for analysis to determine the composition of the fluid. As used herein, the term "fluid" includes liquids, gases, vapors, aerosols and fluids comprising particulates. Embodiments of the sample bag may be used to collect and or store air, vapor, and or gas samples and/or used to collect air, vapor, and or gas samples on a sorbent tube, particulates of a cassette, filter, or other collection media by drawing the air, vapor, and or gas sample through the sorbent tube, cassette, or other collection media. Environmental Protection Agency compliance sampling and industrial hygiene monitoring relies on accurate and reproducible sample techniques and devices to accurately determine and verify the quality of personnel's work environment. For example, samples may be taken from the air in a work environment and the sample then transported to a laboratory for analysis to determine the environmental quality of the sampled air or field samples may be collected and taken to analytical instruments such as, but not limited to, gas chromatographs, infrared analyzer, and mass spectrophotometers for analysis on site. Onsite analysis saves time and money compared to analysis completed at remote locations. The industrial hygiene sampling is used to monitor and ensure a safe work environment for personnel.

Figure 1:
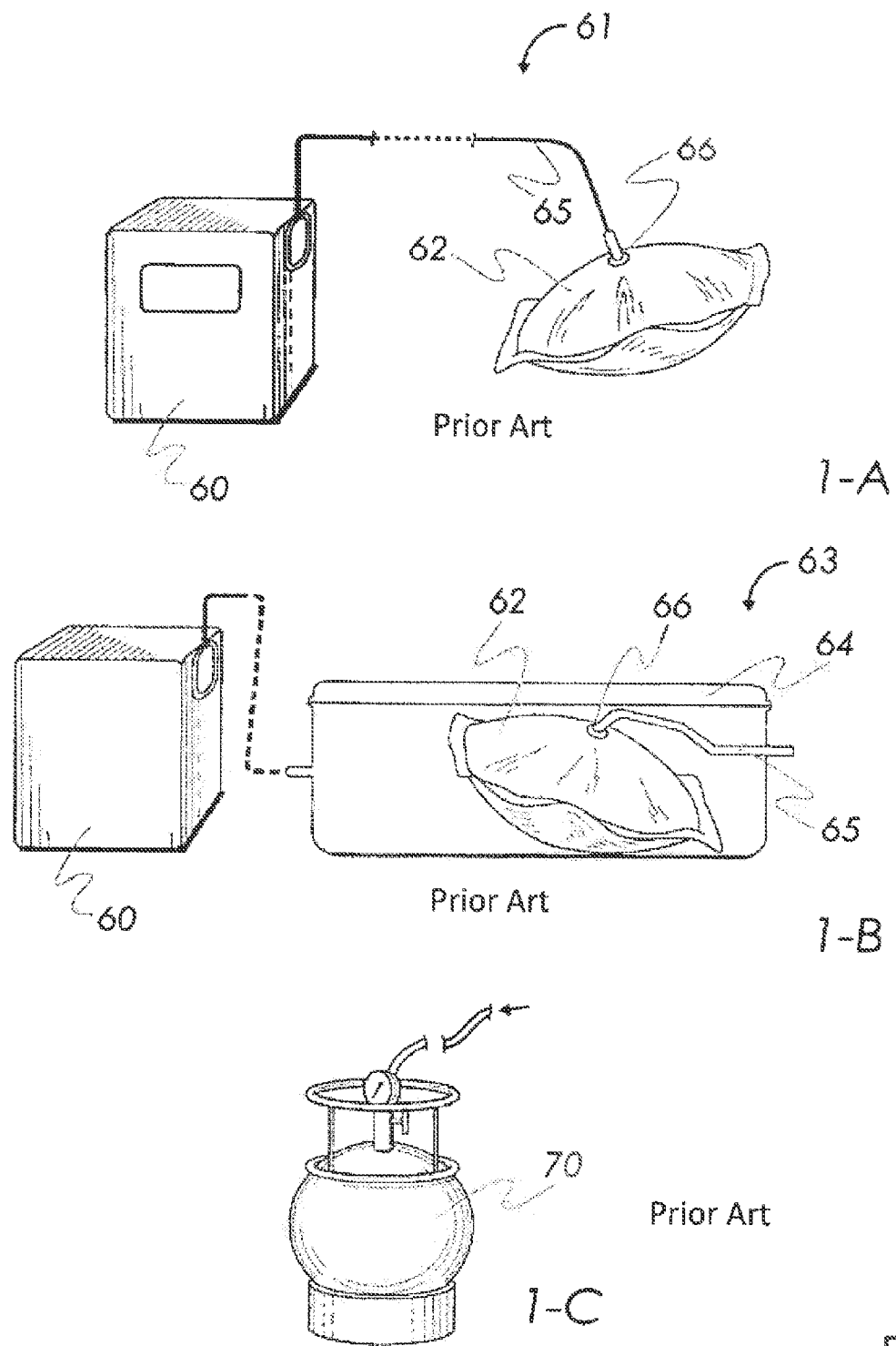
FIG. 1 depicts three conventional sampling devices, wherein FIG. 1-A depicts a conventional direct sampling apparatus capable of direct short or long term sampling comprising a variable speed pump pumping a sample into a gas-sampling bag.

Typical conventional sampling systems comprise a sampling pump as the driving force to pump the gas to be sampled into the sampling bag. See FIGS. 1-A and 1-B. Though these systems work well, sampling pumps are expensive, require frequent maintenance, and may cause contamination of the sample.

Embodiments of the sampling apparatus described herein use gravity, a spring, compressed air, or hydraulic fluid to develop the driving force to cause the gas to be sampled to be drawn into the sampling bag. In embodiments of the sampling device described, the sampling device does not include a sampling pump as a driving force for sampling.

As in conventional sampling systems, embodiments of the sampling devices and systems comprise a sampling container or sample bag. The sampling container may be any container capable of retaining and substantially protecting the integrity of the sampled fluid during sampling, transport and analysis. Embodiments of the sampling apparatus may comprise at least one of sampling activation means. As described above, the activation means may be direct activation or indirect activation. In direct activation, the activation means acts directly on a wall of the sampling container to expand the inner volume of the sampling container and draw a sample into the sampling container. In indirect activation, the activation means acts on a hermetically sealed secondary container comprising the sampling container. (See FIG. 1-B for a conventional indirect activation system and FIG. 7 for an embodiment of a weighted indirect activation sampling process). Even a slight vacuum within the secondary container results in expansion of the volume of the sampling bag and a fluid to be sampled to be drawn into the sampling bag through the inlet of the sample container.

Sample Container

Embodiments of the sampling apparatus described herein comprise a sampling container such as, but not limited to, a sample bag. The sample container may comprise at least one flexible or elastic wall. The flexible or elastic wall of the sample container allows the inner volume of the sample container to be increased thus drawing a fluid to be sampled into the sample container through the inlet. The walls of the sampling container define the inner volume of the sample container. The inner volume of the sampling container may be expanded by application of a force to the walls of the bag to cause the walls to bias apart. The force may be, as described above, a direct force acting of the wall or a vacuum within a secondary container acting upon the walls of the sample container. The sampling container further comprises at least one inlet in fluid communication with the inner volume and an area exterior to the sample container.

The sample container may be a sample bag. The sample bags may be at least partially constructed from any substantially impermeable flexible material such as, but not limited to, polyvinyl fluoride (PVF), FLEXFILM™, FLEX FOIL™, polyvinylidene fluoride (PVDF), polytetrafluoroethylene, metalized films, metal alloys, stainless steel including low carbon stainless steels, flexible sheets of stainless steel, and multilayered films. The sample bags may be as described in U.S. patent application Ser. No. 13/035,163, which is hereby incorporated by reference in its entirety. There are many sample bags available from SKC™, for example. Material for the flexible middle body may be selected from the group of multilayer materials such as multilayer materials comprising aluminum foil between the layers of polyester, Nylon or both and/or a sealing layer comprising a polyolefin. It is advantageous to the present invention for the sample bag to have additional thin inside layer chosen from a group including SST, PEEK, Teflon, Kaynar, Tedlar or alike.

Embodiments of the sample bag comprise at least one thin monolayer or multilayer flexible wall forming an air tight pouch. The sample container or sample bag may comprise a combination of flexible and rigid walls. The sample bag may be made of any desired shape including, but not limited to, circular, oval, square, rectangular or polygonal. Embodiments of the sample bag may be constructed from several walls with seams. The seams may be formed by any effective method including welding, folding, thermo-sealing, and/or adhesives, for example. The body may have two main walls and, optionally, may have additional side walls. It may follow the shape of flat pouch, accordion or randomly folded side walls. Both of the main walls may have one or more apertures for mounted inlet/outlets such as tubing connectors, valves, orifices, and septums, for example.

Embodiments of the sampling device may comprise a sample bag with attached panels. The panels may be similar to the panels described in U.S. patent application Ser. No. 13/028,587, now U.S. Pat. No. 8,714,035, which is hereby incorporated by reference in its entirety. One wall of the sample bag may be considered a top wall. The designation of the top wall is based upon a typical orientation of the sampling apparatus in use. Embodiments of the panel may comprise a panel made from a light sturdy material. The light sturdy material may be a plastic, metal sheet, cardboard, wood, composite material, foam or other material, for example. The sample bag may comprise only one panel, if desired. It is advantageous to this invention if the material of the panel is a corrugated plastic sheet, preferably polypropylene, although it may be any sturdy, relatively thin material, including aluminum or stainless steel sheets. The panel may also be one of the walls of the sampling container. As such, the sample container may have at least one rigid wall in which the flexible wall is connected. The rigid panel may serve both purposes as a wall and a panel, for example. The material of the panels and is advantageously chosen as light rigid corrugated plastic such as polypropylene of 2 to 8 mm in thickness, for example.

In one embodiment, the sampling apparatus comprises panels that have a larger surface area than the flattened sample bag. A panel attached to the sample bag may also comprise an aperture such that the inlet of the sample bag may extend through the aperture, if appropriate.

In another embodiment, the sampling apparatus comprises a sample bag having wall constructed from thin monolayer or multilayer flexible foil (or thin metal sheet) forming a substantially air tight bag with any desired shape. The sample bag may be constructed from several walls. The walls may be connected together with seams, welds, adhesives, heat sealing, compression sealing, combinations thereof, or other sealing means. For example, the sample bag may have two main walls and, optionally, may have additional side walls. The sample bag may be a flat pouch, bellows shaped, accordion shaped or have randomly folded side walls. Both of the two main walls may have one or more apertures, an inlet and inlet valve and septum.

In certain embodiments of sampling devices for gravity activation, the size of one or more panel may be slightly larger than the surface area of the (top portion of the) sample bag. Further, any apertures in the sample bag may be made to match and be accessible through an aperture in a panel. A bottom wall is defined as the wall on an opposite side of the sampling bag as the top wall. Generally for gravity activation embodiments, the top wall of the sample bag will be connected (directly or indirectly) to the hanger element and the bottom wall will be connected (directly or indirectly) to the weight. Therefore, gravity provides the biasing force on the sample bag walls to increase the inner volume of the bag. The hanger element may be a hook, ring, a panel for resting on a support structure, or other means to support the top portion. In other embodiments, the bottom panel may be stationary and the top panel may be moved to draw a sample within the sampling bag.

In specific embodiments for gravity activation, the sampling device comprises a top panel, a bottom panel that has a larger surface area than the bottom wall of the sample bag and smaller surface area than the top panel. This bottom panel comprises a means for attaching a weight in gravity activation methods.

The weight support element may comprise at least one retractable C-shaped handle defining a recess for retaining the weight, may form a substantially enclosed accessible space such as a pouch, may comprise a hook, an adhesive, mechanical connector, hook and loop connector, or may be formed integral to the wall or panel, for example. The weight, in some particular embodiments, may be positioned into inner sampling space. In embodiments of the sampling apparatus comprising a weight support element comprising C-shaped handles, the C-shaped handles may define a recess that may receive a bottle or other container having a predetermine volume or a weight. The container may be filled with any liquid or solid to produce the desired weight. As water is readily available, nontoxic, and has a consistent density, the volume of the bottle may be filled to a known volume corresponding to known combined weight of the container and water. The bottle also may have a means to allow for a complementary connector to attach to the weight support element on the bottom panel or the weight support element on a sample bag wall. In an embodiment with a pouch at the bottom, the pouch may accept any type or shape of weight. In some embodiments, the weight for the pouch or other weight support element may be a metal piece or metal pieces—shims with known size and density, for example, that may be combined to produce the desired total weight. The top panel may be suspended by means of at least one string, wire, rope, ribbon, other elongated member, or a combination thereof to hang the weight, For example, in some embodiments, the sample bag may comprise at least three strings or other flexible supports for connecting the weight to the bottom of the sample bag or the bottom panel of the sampling device.

The hanging element may be hung on any suitable object allowing sufficient space underneath the sampling device in its empty configuration to accommodate the device in its full configuration after the sampling process is completed. The hanging element may be a hook for connecting to the ceiling, a ring capable of being placed over a hook on the wall or ceiling, or other object capable of supporting the total weight of the device. Typically the sampling apparatus has a weight less than 6 lbs. Advantageously, the top panel may be supported by a box or a box-like frame or structure. In one embodiment, the box or box-like frame or structure made from material similar or the same as the panels. Advantageously, the top panel may fit the top of sturdy walled box preferably with transparent walls or window on at least one of the walls. In certain embodiments, the sampling device may be supported by any means capable of supporting the device without operator assistance.

Gravity Activation

In certain embodiments, the sampling process may be activated by allowing the sample bag to expand by the force of gravity on a portion of the sampling device. In embodiments involving gravity activation of the sampling process, the sampling apparatus may comprise a support element and a weight on opposite sides of the sampling bag. The hanging support element is positioned on one side of sampling bag and the weight is positioned on the opposite side. The weight provides a downward force that is transmitted to one side of the sample bag. The support element retains the opposite side in substantially stationary position thus the walls are biased away from each other creating a vacuum within the inner volume of the sample bag thereby causing a driving force for drawing a sample into the bag.

The weight may be removably secured to one side of the sample apparatus, panel or sample bag such that it may be removed and reinstalled or replaced with a different weight or weighting system. In embodiments, the sampling device or sample bag may comprise a weight support element, wherein the weight may be connected to the weight support element. The weight should be of sufficient weight or mass to create a vacuum within the inner volume. The vacuum is the driving force for drawing the gas to be sampled from outside the sample bag into the sample bag. The vacuum can be created by the downward force created by the weight on at least one of the walls of the sampling bag. The rate of expansion of the sampling bag may be determined by the flow rate of the sampled fluid into the sample bag, allowing the inner volume of the sample bag to increase.

The sampling bag may further comprise an inlet flow system. The inlet flow system may comprise at least one of an inlet valve, a flow control device, tubing or other flow conduit, a particulate filter, and optionally, a colorimetric or sorbent tube, colorimetric badge, colorimetric paper indicator, impingers or other desired components.

Embodiments of the sampling device replace sampling apparatuses that require a mechanical pump by using gravity to provide a defined repeatable and reproducible source of power for typical sampling times. In such embodiments, the force provided by the weight is consistent, therefore moderate vacuum created in the inner volume of the device is consistent throughout the sampling process, and the fluid flow rate into the sampling bag may also be consistent. The flow rate depends on the pressure differential between the inner volume of the sample bag and the environment to be sampled and the configuration of the inlet and the components attached to the inlet. As such for similar weights and sampling devices, repeatable sampling times and results are possible and may be obtained.

In one embodiment, the sampling device may comprise tubing attached to the inlet on the top panel or in its proximity. For example, the sampling device may comprise tubing extending the sample point 5 to 6 feet above from the floor and means for its support. In some types of long-term sampling, a sampling inlet point 5 to 6 feet above the floor is recommended to obtain a representative sample of the environment that workers may be exposed to during a work shift or other period.

The sampling devices of the invention with activation by gravity, a biasing force, spring, pressurized fluid, or compressed air as the driving force advantageously avoids the drawbacks of other sampling devices or canister sampling methods. The device is easy to manufacture, transport, and configure at a sampling location for use. The use of sampling devices with activation by gravity, a biasing force, spring, pressurized fluid, or compressed air as a driving force do not require an operator to have significant training or other qualifications to operate the devices to obtain accurate samples and once activated may run unattended without concern of an electrical outage or batteries ding during the sampling period. Further, the sampling apparatus may be placed in a box or other container to protect the device from the corrosive environments or other elements.

The weight may be any object of sufficient weight to create a vacuum within the inner volume by biasing the walls of the sampling container apart. The vacuum provides the driving force for drawing the fluid or gas into the inner volume of the sample bag. Embodiments of the weight may be a metal weight, a container, bottle or other reservoir, stone such as granite, marble, or other material of sufficient weight. The container, bottle or other reservoir may be filled with a material. The type of material, amount of material in the container, bottle, or other reservoir will determine the weight of weight and therefore affect the vacuum in the inner volume and the driving force of the sampling process. The bottle, container, or other reservoir may filed or partially filled with water, sand, earth, gravel, and/or metal objects to produce the desired weight. The bottle, container, or other reservoir may comprise graduation marks on the container to be used to accurately fill the bottle, container or other reservoir to the desired level. The weight should be sufficient to create a desired flow rate of the gas to be sampled through the inlet. For example, the weight may be greater than 100 grams. In some embodiments, the weight may have a weight greater than 500 grams. In other embodiments, the weight may have a weight between 500 grams and 6000 grams. In other embodiments, the weight may have a weight between 500 grams and 6000 grams or wherein the weight has a weight between 500 grams and 8000 grams.

The purpose of the weight is to create the driving force for sampling. In specific embodiments, the weight is capable of creating a vacuum within the inner volume of the sample container or sample bag from one inch of water to eight inches of water pressure below atmospheric pressure. In other embodiments, the weight is capable of creating a vacuum within the inner volume of the sample container or sample bag from two inch of water to six inches of water pressure below an atmospheric pressure. In cases with reduced pressure sampling, additional weight may be added to create sufficient vacuum to draw a sample fluid into the inner volume of the sample bag.

Support Element

The sampling device may comprise a support structure capable of supporting the sampling device. The support element may be any mechanism that holds the top portion, top wall of the sample bag, or top panel stationary relative to the bottom wall. In embodiments, the sampling device comprises a support element comprising a hole or eyelet, a hook, a panel, hook and loop connectors, wire or string, hanger, support structure such as a frame or box, combinations thereof or other hanging element, for example.

Figure 3:
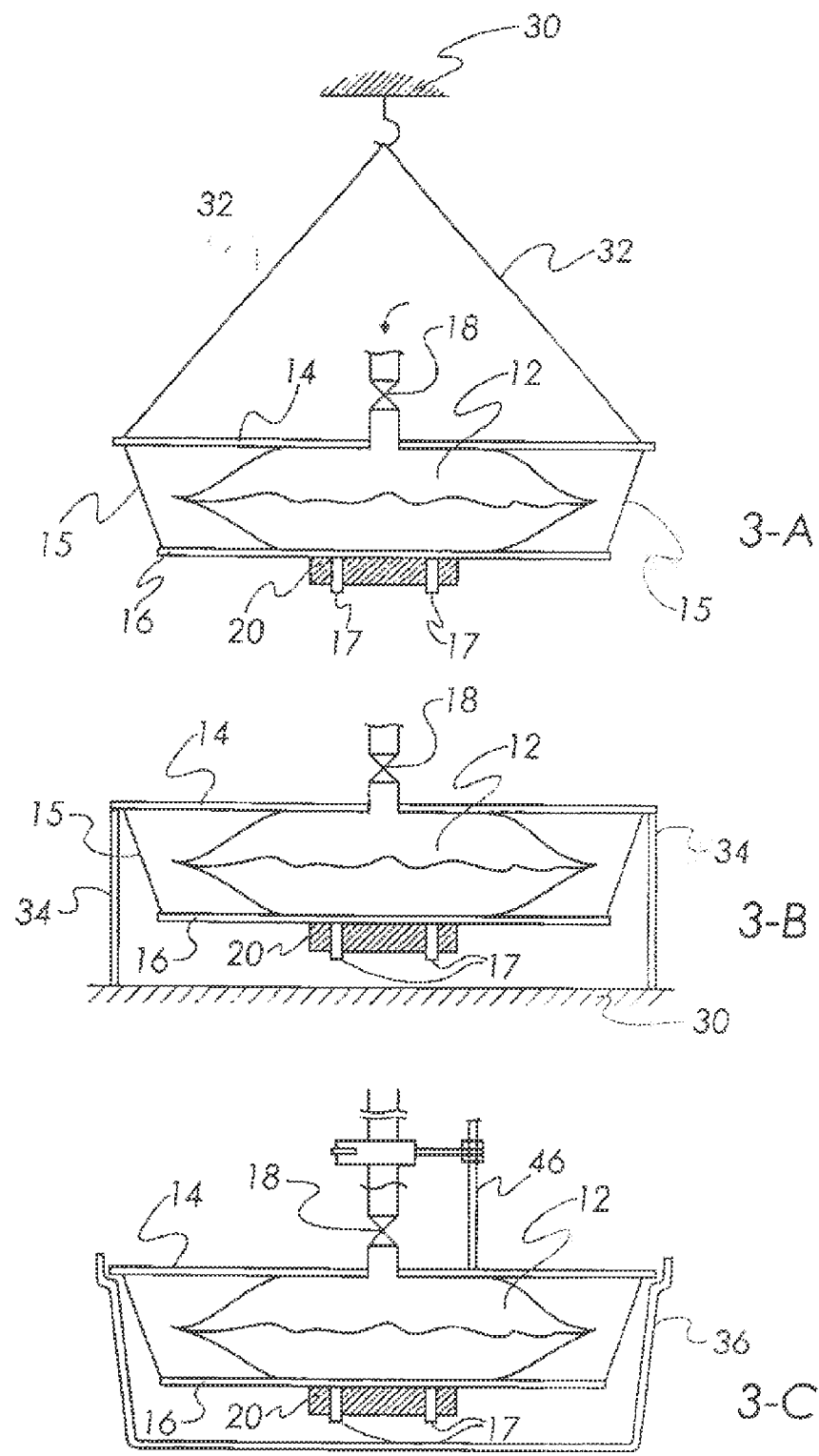
FIG. 3 depicts embodiments of three sampling devices, wherein FIG. 3-A depicts an embodiment of a sampling apparatus comprising a sample bag, a weight sufficient to create a vacuum within the inner volume; a hanging element connected to a panel attached to a top wall of the sample bag.

In one embodiment, the sampling device may comprise a box or box-like frame ("box") to support a top panel of the sample bag as shown in FIG. 3-C. The sample bag with a weight may be suspended within the box. The box may comprise an open section or a transparent portion so the sample bag may be seen from outside the box and the sampling process may be monitored. The box may further comprise a lid defining an aperture for receiving the inlet. In another embodiment, the lid may be the top panel of the sample bag.

In other embodiments, hanging element comprises a panel and a hook, a panel capable of supporting the sampling bag within the box, the box comprises side walls and the panel is supported adjacent to a top opening of the box on the side walls, or other support element, for example.

Inlet

The sample bag or sample container comprises an inlet. The inlet provides fluid communication between the inner volume of the sampling bag and the environment to be sampled. As the inner volume is expanded by the activation force, the fluid to be sampled flows through the inlet into the inner volume.

The inlet may have other components attached to the inlet. Embodiments of the sample device comprise an inlet system. The inlet system may comprise one or more of a tubing connection, a valve, a flow control device such as a flow restrictor, a septum, a colorimetric tube, and/or other components. The valve may be an ON/OFF valve or comprise flow control features and may comprise connection means for tubes and/or a build in septum. In case wherein the inlet system has a septum, the sample bag would not need an additional inlet comprising a septum. In case when the inlet system has a connection means for tube, a second aperture on the sampling bag may be fitted with separate septum.

A tube connection at the inlet is one means for connecting a flow restrictor to on the inlet system for various long-term sampling periods. Certain flow restrictor imposes aerodynamic resistance to the flow through the valve to allow a maximum flow rate into the sampling bag.

Flow Control Device

In some sampling operations, certain flow rates are desired over an extended period of time to provide a long term sample. In such embodiments, a flow control device in fluid communication with the inlet and a gas to be sampled may be attached to the sampling bag. The flow control device will restrict the flow rate of the gas to be sampled into the sampling bag allowing a long term sampling method to be performed. The flow control device could be a restrictor plate or orifice, tubing with a small diameter, tubing comprising a flow restriction such as a porous inert material and/or a membrane/needle mechanism automatically maintaining certain flow.

The flow control devices may be matched with the volume of the sampling bag to provide a long term sample process. The long term sampling process may comprise continuous sampling for standard periods of time such as 15 minutes, 30 minutes, one hour, four hours, eight hours (a typical work shift) or more, such as 24 hrs., which may be typical for home air sampling and new building air testing. Of course, a sampling process of many different desired sample periods may be performed by choosing an appropriate sample bag volume and flow controller such that the sample bag will not be completely filled prior to the end of the sample period. For example, an eight hour sample may be taken in a one liter sample bag if the flow rate into the sample bag is controlled to less than 125 ml/hour (1 liter/8 hours). The flow control device in this particular invention is advantageously chosen as a flow restriction device with minimum surface in contact with the sampled gas therefore negligible sorption of the target gases occurs.

Flow Restriction Devices

A flow restriction device may be fabricated from highly corrosion resistive material with low sorption and low permeability. Such material may be stainless steel, some plastics, quartz or special glass preferably a silanized glass. It is advantageous for present invention to use as restrictor a capillary fabricated by plastic such as PEEK (polyether-ether-ketone). The inside diameter of the capillary or orifice, the length of the capillary, the volume of the sampling device and the pulling force (weight) or reduced volume define the sampling flow rate. For a given sampling volume and fixed weight, the inner diameter and the length of the capillary define the sampling flow rate and sampling time. It is advantageous to the present invention to operate mainly with two geometrical parameters—length (L) and internal diameter (ID) of the capillary for calibrating the sampling time. Another option is to change the weight (changing for example the volume of the water in the appropriately graduated bottle) is also possible to change the reduced pressure in the inner volume. By these methods, sampling times may be varied from less than one minute to 5 minutes which is practically a grab-sampling process and all set (from some sampling standards times)—15 min (STEL), 30 min, Ceiling, 1, 2, 4, 8 hrs. representing a portion or a full working shift or 24 hrs. (House environment—building standards) may be achieved by the use of properly calibrated flow restrictors and weights. The invention suggests a set of interchangeable precalibrated flow restrictors to be part of ultimate set sampling apparatus.

Particulate Filter

It may be advantageous to have a particulate filter from sintered quartz, glass, plastic, very fine mesh (over 300×300 lines per inch) of stainless steel, nylon, polyester or fluoropolymer between the restricting capillary and sampled environment in order to avoid plugging the capillary by accumulation of airborne particulates.

When a valve in the inlet system is in fully open position "ON." the weight is pulling down the bottom panel and/or the bottom wall thereby creating a moderate vacuum in the body. The sampled fluid or gas is drawn into and filling the inside volume either partially or to its maximum available volume.

Volume Limiting System

The sampling device or sample bag may comprise a volume limiting system. For example, mechanical means may limit the final expansion of the sampling bag, the mechanical means include strips, strings, chains, solid posts, or devices that are capable of limiting a distance between the panels. The mechanical means may be attached between the top and bottom panels or connected between the walls of the sampling bag. The volume limiting system may mechanically restrict the device from being filled to its full volume. The volume limiting system limits the sampling volume and also protects the flexible walls from forming wrinkles and potentially pinholes in the stress points of those wrinkles. The volume limiting system may have optional means to be engaged during the sampling procedure and may be disengaged during shipment thereby allowing the volume to expand if the sample is airborne mailed at high altitude where the pressure difference may lead to rupturing the sample bag.

Spring Activation

In other embodiments of the sampling apparatus, the panels and/or sample walls are biased by at least one spring. In specific embodiments, the springs are interior to the inner volume of the sample bag and bias the panels apart to create a vacuum within the sample bag. In some embodiments, the spring may be small compressed spring or a crest-to-crest spring.

The sample apparatus may comprise at least one spring external to the sample bag and bias elements that are attached to the walls of a sample bag. For example, the sample bag may have panels attached to opposite walls of the sampling bag and the springs may be attached between the panels to bias the panels apart.

Compressed Gas Activation

In another embodiment of the sampling apparatus, the panels and/or sample walls are biased by at least one pneumatic cylinder or otherwise biased by compressed gas. In specific embodiments, the pneumatic cylinders are exterior to the inner volume of the sample bag and bias the panels apart to create a vacuum within the sample bag. Another embodiment, the sample device may comprise pneumatic or hydraulic cylinders or other tube like pneumatic inflatable device situated exterior to the sample bag secluded between the two panels. Once the tube like device is inflating the panels are biased creating vacuum into the sample bag.

Other embodiments may include at least one hydraulic cylinder.

Secondary Container

Other embodiments include an indirect activation system wherein the weights, springs or pneumatic or hydraulic cylinders act on walls of a hermetically sealed secondary container with changeable volume comprising a sample bag. By indirect or direct activation, the walls of the secondary container are biased apart to create a vacuum within the secondary container and bias the walls of the sample bag apart. The reduced volume in the secondary container acts on the walls of the sample bag to draw a sample into the inner volume of the sample bag.

EXAMPLES

Figure 2:
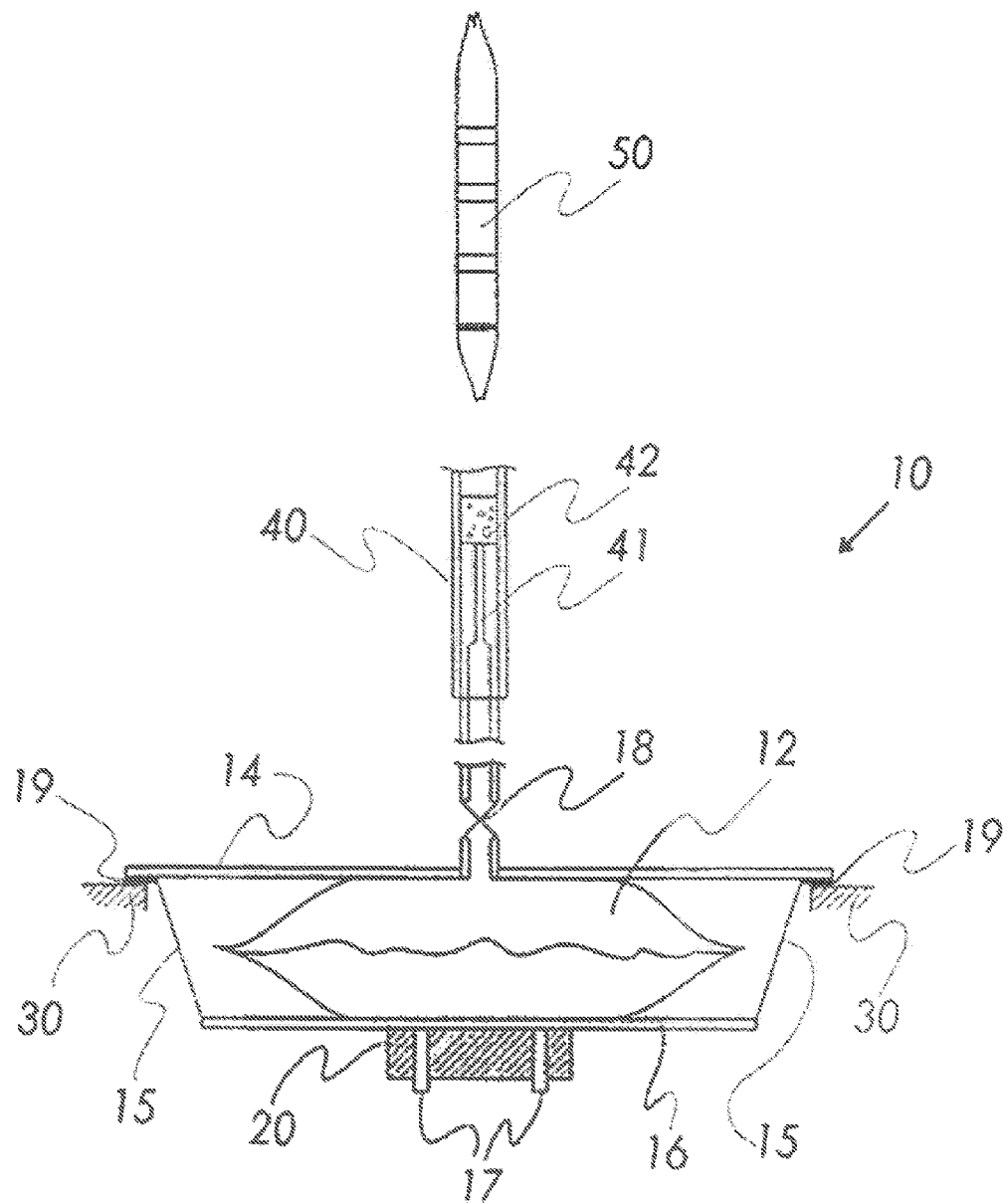
FIG. 2 depicts an embodiment of a sampling apparatus comprising a sample bag and a weight sufficient to create a vacuum within the inner volume thereby utilizing gravity as energy source as well as additional sampling devices including colorimetric tubes and flow devices.

An embodiment of sampling apparatus is shown in FIG. 2. The embodiment of the sampling apparatus may be used to obtain a grab sample or a sample over an extended period of time. The sampling apparatus 10 comprises a sampling bag or middle body defining an inner volume 12, a top panel 14, bottom panel 16, a weight support element 17 and weight 20. The top panel 14 is supported and resting between supports 30. The supports 30 maintain the top panel 14 in a substantially stationary position before and during the sampling process. In this embodiment, the top panel 14 has a larger surface area than the bottom panel 16 and the flexible middle body or sample bag 12 of the device. The middle body or sample bag 12 in a deflated state may be bigger or smaller than the bottom panel 16. The bottom panel 16 and weight 20 may be lowered through the gap between the supports 30 and the top panel 14 will rest upon the supports 30. The weight 20 may be fixed on the bottom panel 16 by weight support element 17. The sampling volume is prevented from expanding to its potential maximum volume by limiting straps 15 that extend between the top panel 14 and bottom panel 16. There is optional means for engagement and attaching the top panel 14 to the support element 30 when sampling. The attachment elements 19 may be adhesive, hoop and loop connectors, pin and hole, screws or other devices to at least temporarily secure the sample bag to the support element. The weight 20 provides a downward force exerted on the bottom panel 16 and the walls of the sample bag 12. The top panel 14 is adhered to the top wall of sample bag 12, the pulling force exerted by the weight 20 stretches the middle body 12 creating a moderate vacuum within the inner volume. The moderate vacuum is a driving force for the ambient fluid to fill the middle body 12 through the inlet valve 18. For short-term sampling the valve 18 may be fully opened. For long-term sampling the inlet valve 18 may be connected to a flow restrictor assembly 40. In case of long-term sampling, the sampling flow rate is restricted by the critical orifice or limited orifice. In specific embodiments, the orifice may be a cross-section of aperture within a thin capillary 41 of inert material. The capillary may be made, for example, of any stainless steel, Teflon, PEEK, fluoroplastics or similar material. Based upon the desired fluid flow and the size of the weight, the inner diameter of the capillary may be from 1.0 micron to 3.0 micron and length of the capillary anyone from 1 mm to 100 mm, for example. Other lengths and sizes may also be appropriate in certain applications.

Figure 5:
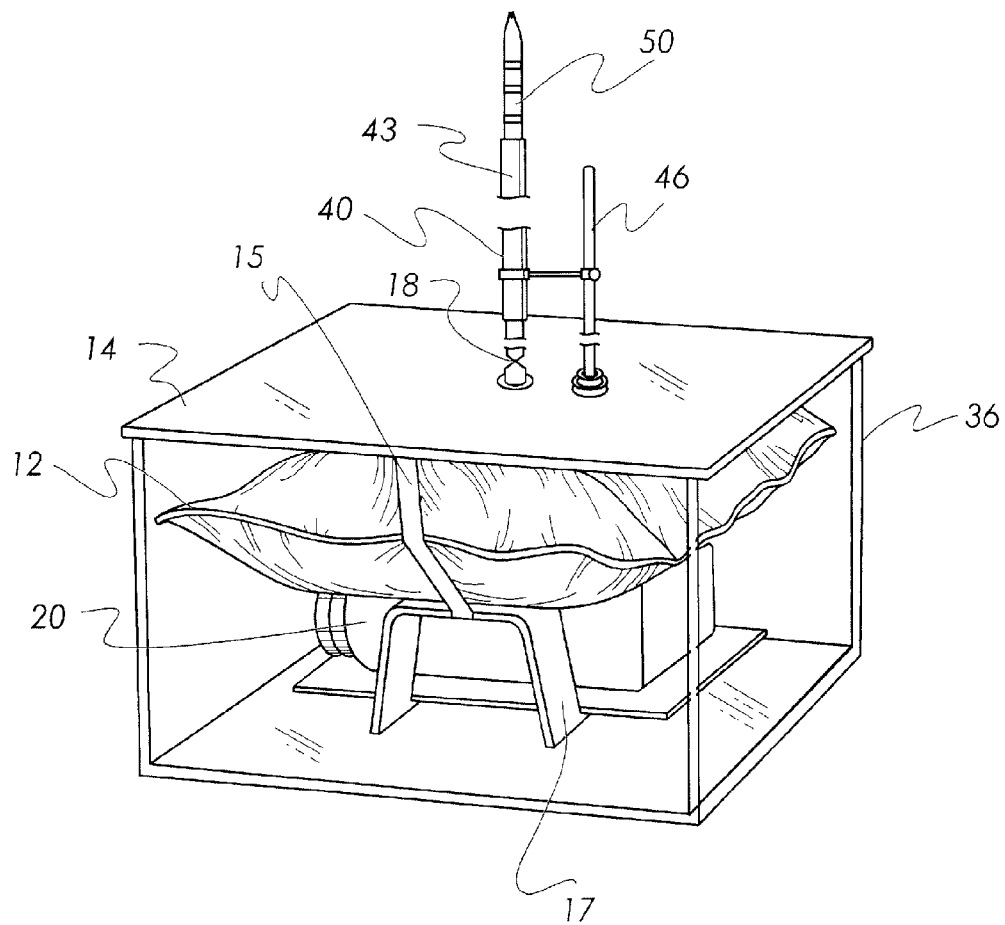
FIG. 5 depicts a perspective view of a sampling apparatus with a partial cross-section of the supporting box, the sampling device and a bottle or other reservoir which may be filled to provide the desired weight and sampling time.

The bottom panel 16 advantageously has a weight support element 17 for accommodating a weight 20. The support elements 17 as shown in FIG. 2 comprise retractable brackets or handles 17 (85 in FIG. 7) which may form an appropriate channel (also shown on FIG. 5) for receiving a weight 20. The generic weight 20 may be a flat piece of metal with known weight or may be an empty vessel filled by materials having a known density adjusted to a known total weight. The weight 20 may be advantageously a plastic bottle 20 (as shown in FIG. 5) with volume graduations marked on a wall and filled with aforementioned materials and capped with hermetic lid. The shape of the bottle 22 may be rectangular and adjusted to fit the channels formed by retractable brackets 17. The bottle 22 may have additionally means for better adjustment into brackets 17 as well as means for reading the inserted volume of liquid or dry material—graduation. To commence the sampling process, valve 18 may be opened at least partially and, once the sampling process is completed, the valve 18 may be closed. The volume limiting straps 15 prevent the device to be filled to its maximum possible volume for two general reasons; to prevent the formation of side wrinkles which may create stress points and to allow additional expansion by changes of ambient pressure such as during transportation via airmail. Straps 15 may be disengaged by Velcro adhering points before the sampling device 10 bag is airmailed thereby to allow the device to extend its volume and compensate for the altitude depending pressure drop.

FIG. 3 depicts three possible support elements for embodiments of the sampling apparatus. FIG. 3-A shows the device 10 hung from a wire 32 from a hook attached to a ceiling or other elevated object 30. Such a support element may have one or more wires or strings 32. The embodiment shown has four strings 32 that may be adjusted to keep the entire sampling device 10 substantially horizontal. FIG. 3-B shows the sampling device 10 supported by side walled box-like frame 34. Such construction may be executed from the same type corrugated plastic as the material for the side panels or may be any other structurally supportive material such as plastic, cardboard, or metal. The side supporting walls 34 may form a foldable construction which assures the device 10 is held substantially horizontal during the sampling process. FIG. 3-C comprises an embodiment of the sampling apparatus with side supports on a plastic box 36 wherein top panel 14 of the sampling device acts as a lid for the box 36. Advantageously an additional lid comprising an aperture for receiving valve 18 may be placed over the top panel 14 which allows this lid to be secured or locked preventing interference with sampling process. This lid advantageously may have a means 46 for supporting the extension of a sampling tube to a higher sampling point (some sampling process may comprise a structure for supporting the sampling point about 6 feet above the floor). The embodiments of the invention shown on FIG. 2 and FIG. 3 are using gravity to create a moderate vacuum within the sample container. The sampling apparatus may also be used in conjunction with additional components such as, but not limited to, detector tubes or sampling tubes of long duration or TWA sampling tubes, sorbent tubes, colorimetric tubes or badges or impingers, cassettes or filters, for example. The additional components may be attached to the inlet to draw a sample fluid through the additional components.

Figure 4:
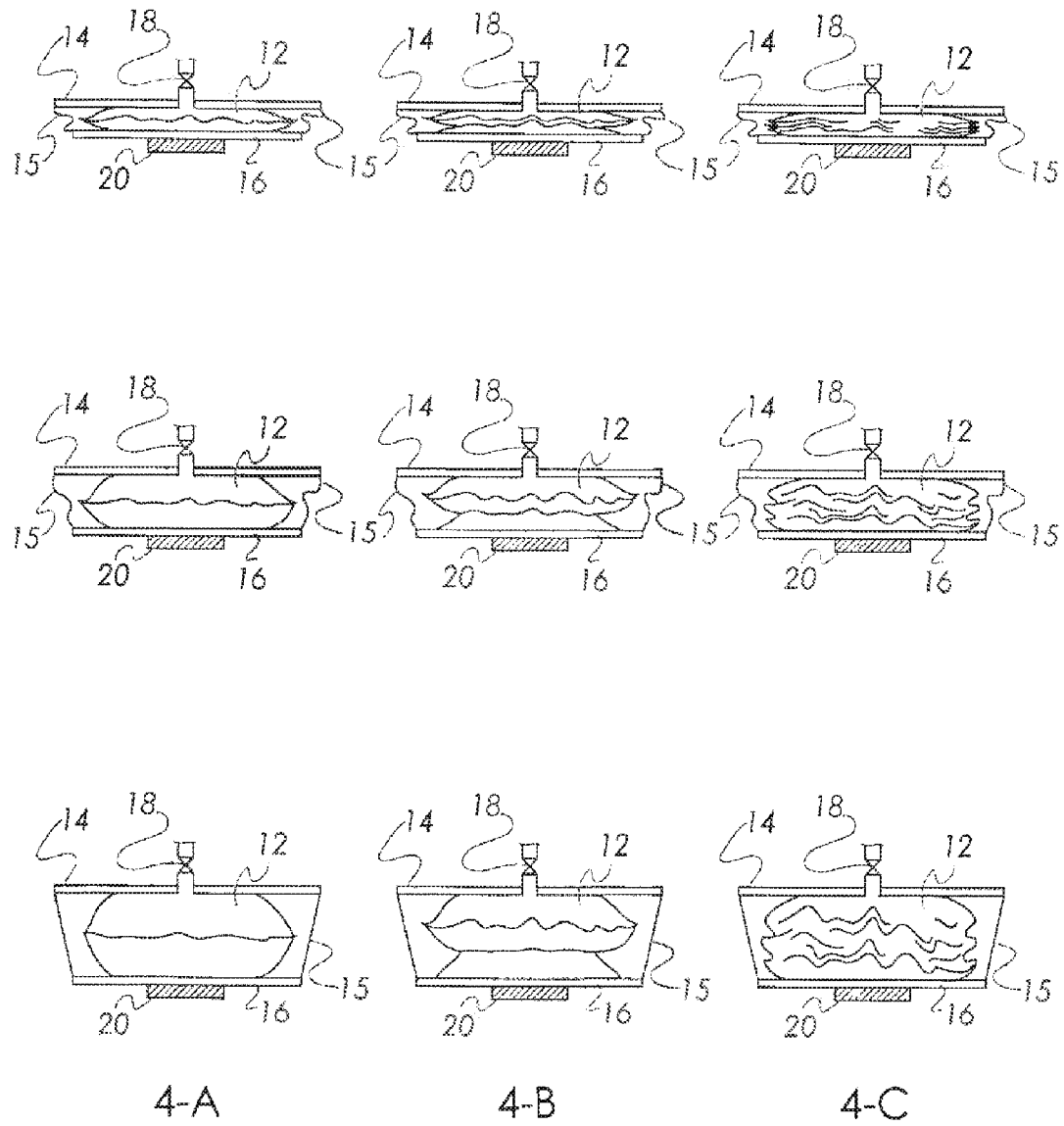
FIG. 4 depicts three sampling devices with volume limiting devices in various stages of sampling with different shapes and/or styles of the sample bags, wherein FIG. 4-A depicts a sampling apparatus comprising a regular type bag with two symmetric flexible sides.

FIG. 4 depicts various embodiments of sampling apparatus in various states of sampling. The embodiments have different shapes and styles of the sample container 12; such as a pouch, FIG. 4-A; accordion type, FIG. 4-B; or a sample container with randomly folded side walls, FIG. 4-C. The sample container with randomly folded side walls or accordion style walls may be advantageously used as a sampling pump for auxiliary devices—sampling tubes, colorimetric tubes, filters etc. The devices are shown depicting a sampling process in three stages of container volume, beginning, advanced and complete (complete sampling volume is a big portion but not the entire maximum volume of the sample body 12 due to the limiting elements 15).

FIG. 5 depicts an embodiment of the sampling device 12 comprising the sample apparatus mounted in a box 36. The box 36 may be of any supportive material such as, but not limited to, cardboard, plastic, metal or a combination thereof, for example. Further, at least a portion of box 36 may be made from transparent material such as acrylic, polycarbonate, polyolefins, etc., and may have transparent walls allowing observation of a sampling process.

Since at least a portion of the box is transparent, the sampling process may be observed and corrected if it was improperly set up or defects in the sample bag 12 have developed or the sampling period is complete. On the top of the box the top panel may be covered additionally with a lid and on the lid a supporting means 46 for extension tube 43 may be mounted. Thus, the extension tube 43 may extend approximately five to six feet above the floor into a "breathing zone" as defined by OSHA. An extension tube 43 end may be connected to auxiliary sampling devices such as sampling or colorimetric tube 50, impingers, and filters or alike.

Figure 6:
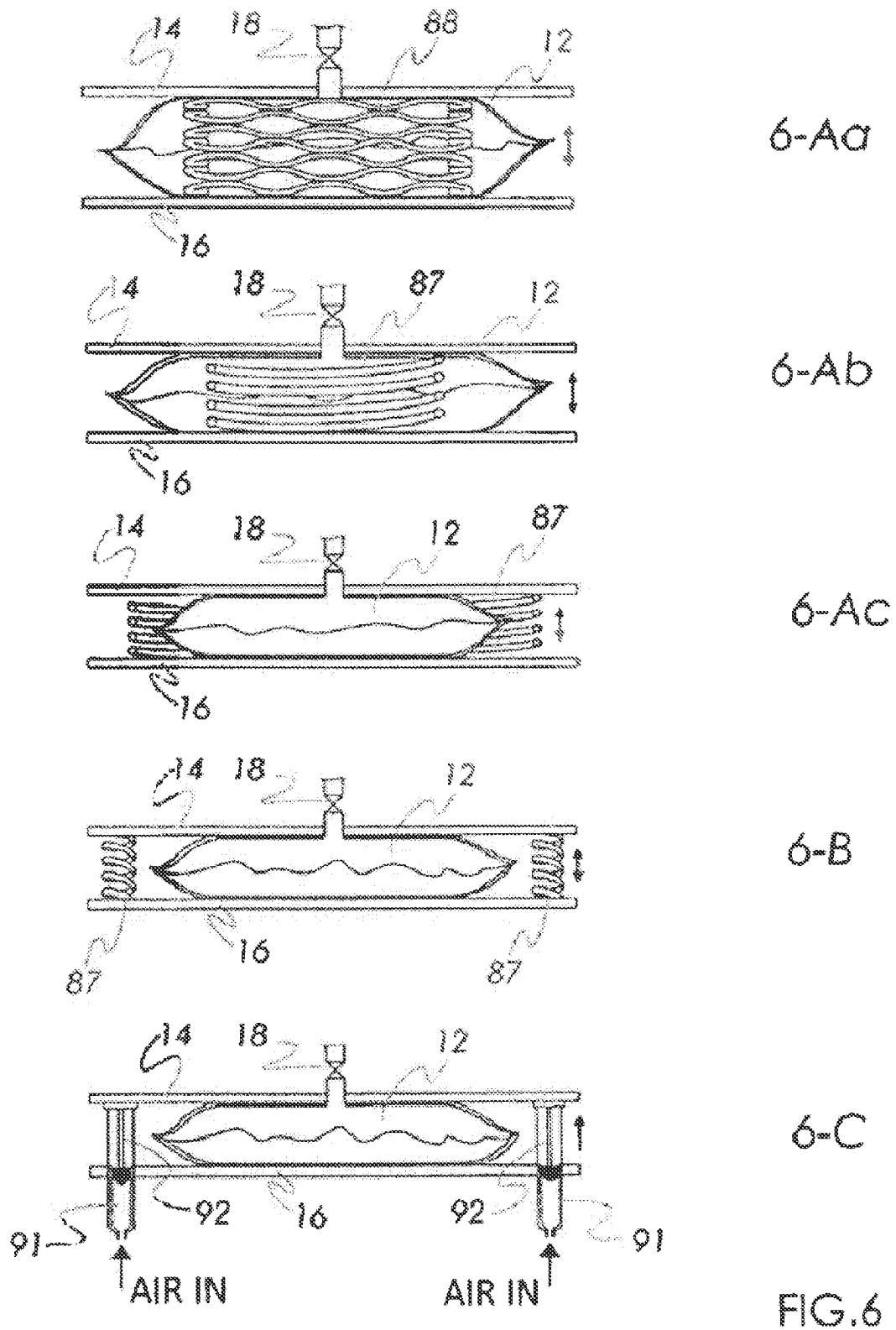
FIG. 6 depicts embodiments of the sampling apparatus utilizing force different than gravity to bias the bag's walls; wherein FIGS. 6-Aa and 6-Ab show the use springs mounted within the sample bag.

FIG. 6-Aa depicts a sampling device wherein a spring 88 is a crest-to-crest type mounted into the interior of the sampling bag and the springs provide the driving force between the two hard walls—panels 14 and 16 to create moderate vacuum. The crest-to-crest springs can be coated with a nonadsorbing coating (such as Silcocoat) and such springs have a very short height when compressed in a flat sampling bag.

In FIG. 6-Ab, an embodiment of the sampling apparatus comprising a spiral spring 87 is used which may be used for sampling of gases that will not significantly adsorb on the material of the spring mounted inside the sampling bag. In another embodiment shown in FIG. 6-Ac, the sampling apparatus comprises a spiral spring 87 mounted outside sampling bag to bias the panels 14 and 16 apart. As large diameter springs, as shown in FIG. 6-Ac, may have a greater weight, an embodiment of the sampling device may comprise a plurality of springs 87 as shown in FIG. 6-B. The sampling device comprises a plurality of springs 87 (at least two) wherein the springs may be mounted in close proximity to the bag's exterior in order to provide biasing forces on the panels 14 and 16 therefore to create moderate vacuum into the sample bag. In some embodiments, it is advantageous for the springs to be crest-to-crest type in order to accommodate in a small gap between the panels 14, 16 when sampling bag is flattened and empty. Other types of exterior mounted springs, such as spiral or flat scissors type also may be used if constructively satisfy the requirements to be accommodate a small space or otherwise to provide biasing forces.

FIG. 6-C displays the use of pressurized gas used in pneumatic cylinders. At least two gas pressure cylinders 91 may be mounted in close proximity around the sampling bag's perimeter. Once the pressurized gas acts on the cylinder 91 and piston 92 it biases the side panels 14 and 16 apart and acts as described heretofore. The cylinders may be open and used as pneumatic movers or closed under pressure and used as gas-springs. Hydraulic cylinders may similarly be used.

FIG. 6-Da-Dc depict a sampling apparatus comprising and inflatable bladder 94 that may by inflated with a pressurized gas. In the embodiments of the sampling apparatus shown, the inflatable body surrounds the sampling bag biasing panel surfaces apart while being inflated. When the bag is flattened, the surrounding inflatable body is also flattened. Once the pressurized gas starts inflating the bladder 94, it provides biasing forces on both panels 14 and 16 offering the sampling process the same as described heretofore.

Figure 7:
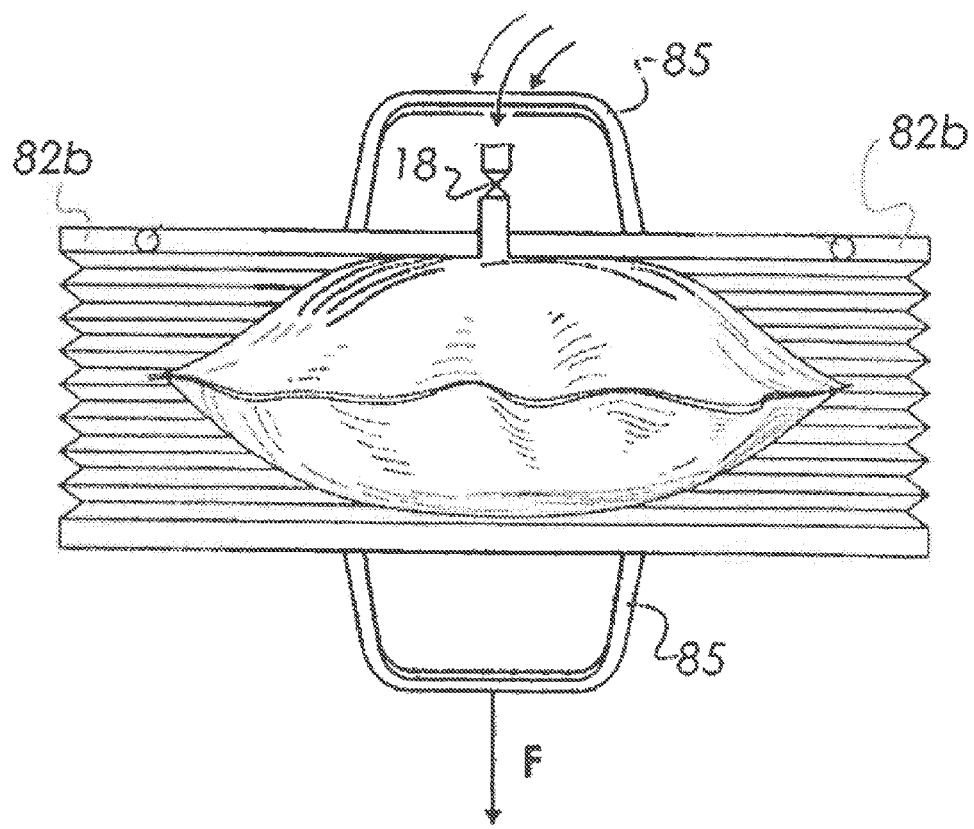
FIG. 7 depicts the use of lung box type container comprising two rigid walls and at least one expandable (accordion type) wall which comprises a sampling bag, wherein the rigid walls may be biased by the force of gravity, springs, hands, compressed gas, or hydraulic fluid.

FIG. 7 displays a sampling device comprising indirect activation of the sampling process. In this embodiment, a sampling bag 62 is contained within an external container. This container may have at least one rigid wall 82b and at least one soft accordion type side wall 83. The embodiment of the sampling apparatus shown in FIG. 7 comprises a container having two rigid walls 82b and 84. Biasing of the rigid walls 82b and 84 away from each other and expansion of the soft wall 83 creates moderate vacuum inside of the container. This vacuum is acting on the bag's walls by pulling them apart and therefore creating a separate vacuum within the sample bag. Advantageously, the container walls may be made transparent for better observation of expansion of the sample bag 62. The container walls of the sampling apparatus of FIG. 7 may be biased by any means described for other embodiments of the sampling apparatus, such as, but not limited to, gravity by attaching a weight to the bottom of the container, springs, pneumatic cylinders and/or hydraulic cylinders.

The sampling device upon present invention has plurality of advantages compared with all state of the art devices and related strategies of sampling. As mentioned advantages are in comparison with two main existing groups of devices and methods associated with them, it is reasonable to provide comparison between device upon invention and each of the existing groups and methods.

The embodiments of the described sampling apparatus and methods are not limited to the particular embodiments, components, method steps, and materials disclosed herein as such components, process steps, and materials may vary. Moreover, the terminology employed herein is used for the purpose of describing exemplary embodiments only and the terminology is not intended to be limiting since the scope of the various embodiments of the present invention will be limited only by the appended claims and equivalents thereof.

Therefore, while embodiments of the invention are described with reference to exemplary embodiments, those skilled in the art will understand that variations and modifications can be effected within the scope of the invention as defined in the appended claims. Accordingly, the scope of the various embodiments of the present invention should not be limited to the above discussed embodiments, and should only be defined by the following claims and all equivalents.

The invention claimed is:
1. A sampling apparatus, comprising:
   a sampling bag comprising:
      an inner volume defined by walls of the sampling bag, wherein the walls comprise at least one flexible wall;
      an inlet in fluid communication with the inner volume;
   a hanging element connected to the sampling bag;

a weight support element connected to the sampling bag; and a weight connected to the weight support element, wherein the weight is sufficient to create a vacuum within the inner volume.

2. The sampling apparatus of claim 1, comprising a flow control device in fluid communication with the inlet and a fluid to be sampled.

3. The sampling apparatus of claim 1, comprising a support structure capable of supporting the sampling bag by the hanging element.

4. The sampling apparatus of claim 3, wherein the support structure is a box.

5. The sampling apparatus of claim 4, wherein the box comprises a transparent portion.

6. The sampling apparatus of claim 4, wherein the hanging element comprising a panel capable of supporting the sampling bag within the box.

7. The sampling apparatus of claim 6, wherein the box comprises side walls and the panel is supported adjacent to a top opening of the box on the side walls.

8. The sampling apparatus of claim 4, wherein the box comprises a lid defining an aperture for receiving the inlet or a fluid conduit in fluid communication with the inlet and the hanging element is connected to the lid.

9. The sampling apparatus of claim 1, wherein the weight comprises a bottle containing water.

10. The sampling apparatus of claim 1, wherein the weight comprises a reservoir.

11. The sampling apparatus of claim 10, wherein the reservoir is filled with at least one of water, sand, earth, gravel, or metal objects.

12. The sampling apparatus of claim 1, wherein the weight is sufficient to create a desired flow rate of the fluid to be sampled through the inlet.

13. The sampling apparatus of claim 12, wherein the weight has a weight eater than 100 grams.

14. The sampling apparatus of claim 12, wherein the weight has a weight between 500 grams and 6000 grams.

15. The sampling apparatus of claim 1, wherein the inlet comprises a valve.

16. The sampling apparatus of claim 1, wherein the hanging element comprises a panel and a hook.

17. The sampling apparatus of claim 1, wherein the hanging element comprises a ring and a panel.

18. The sampling apparatus of claim 1, wherein the weight is capable of creating a vacuum within the inner volume, wherein the vacuum is from one inch of water to ten inches of water pressure below atmospheric pressure.

19. A method of sampling, comprising:

attaching a weight to a bottom portion of a sampling bag, wherein the sampling bag comprises at least one flexible wall, an inner volume, an inlet in fluid communication with the inner volume and a fluid exterior to the sampling bag, wherein a flow control device is attached to the inlet and a support element is connected to the sampling bag; and suspending the sampling bag from the support element to allow the weight to cause an increase in the size of the inner volume of the sampling bag thus drawing a sample into the inner volume through the inlet.

20. The method of claim 19, wherein the sampling bag comprises a valve and the method comprises opening the valve.

21. The method of claim 19, wherein suspending the sampling bag comprises suspending the sampling bag within a box.

22. The method of claim 21, further comprising placing a lid on the box, wherein the lid defines an aperture aligned with the inlet.

23. The method of claim 22, wherein the inlet extends through the aperture.

24. The method of claim 22, comprising securing the lid to the box to prevent tampering with the sampling bag.

25. The method of claim 19, wherein the sampling bag comprises a top panel and a bottom panel, wherein the support element is connected to the top panel and the weight is attached to the bottom panel.

26. The method of claim 19, wherein the weight comprises a bottle containing water and the method comprises adding water to the bottle.

27. The method of claim 19, wherein the weight comprises a reservoir.

28. The method of claim 27, wherein the reservoir comprises graduation markings indicating various volumes of the reservoir.

29. The method of claim 27, wherein the reservoir is filled with at least one of water, sand, earth, gravel, or metal objects.

30. The method of claim 27, wherein the weight has a weight greater than 100 grams.

31. The method of claim 27, wherein the weight has a weight between 500 grams and 8000 grams.

32. The method of claim 27, wherein the weight has a weight greater than 500 grams.

33. The method of claim 27, wherein the weight has a weight between 500 grams and 6000 grams.

34. The method of claim 19, wherein the weight is sufficient to create a desired flow rate of the fluid to be sampled through the inlet.

35. The method of claim 19, wherein the weight has sufficient mass to draw a sufficient quantity of fluid to be sampled into the inner volume.

36. A sampling apparatus, comprising:

a sampling bag comprising an inner volume defined by walls of the sampling bag, wherein the walls comprise at least one flexible wall, an inlet in fluid communication with the inner volume, wherein a hanging element is attached to the sampling bag and a support element is connected to the sampling bag;

a weight connected to the weight support element, wherein the weight is sufficient to create a vacuum within the inner volume; and a flow control device in fluid connection with the inlet and a fluid to be sampled.

* * * * *